(12) United States Patent
Tonomura

(10) Patent No.: US 8,608,701 B2
(45) Date of Patent: Dec. 17, 2013

(54) PUNCTURE NEEDLE FOR ENDOSCOPE

(75) Inventor: Masatoshi Tonomura, Tokyo (JP)

(73) Assignee: Olympus Corporation (JP)

( * ) Notice: Subject to any disclaimer, the term of this patent is extended or adjusted under 35 U.S.C. 154(b) by 124 days.

(21) Appl. No.: 11/750,433

(22) Filed: May 18, 2007

(65) Prior Publication Data

US 2007/0225646 A1 Sep. 27, 2007

Related U.S. Application Data

(63) Continuation of application No. PCT/JP2005/020418, filed on Aug. 11, 2005.

(30) Foreign Application Priority Data

Dec. 21, 2004 (JP) ................................. 2004-369573

(51) Int. Cl.
*A61M 5/178* (2006.01)

(52) U.S. Cl.
USPC .................................................. 604/164.01

(58) Field of Classification Search
USPC ............ 604/164.06, 164.01, 171, 158, 93.01, 604/264, 164.02, 164.07, 164.12, 167.06, 604/523, 117, 48, 272; 600/104, 106, 564, 600/565, 566, 567, 576; 606/46
See application file for complete search history.

(56) References Cited

U.S. PATENT DOCUMENTS

| | | | | |
|---|---|---|---|---|
| 4,181,131 | A * | 1/1980 | Ogiu ................................ | 606/47 |
| 4,532,935 | A * | 8/1985 | Wang ............................. | 600/566 |
| 4,791,937 | A * | 12/1988 | Wang ............................. | 600/565 |
| 4,861,341 | A | 8/1989 | Woodburn ..................... | 604/175 |
| 5,601,588 | A * | 2/1997 | Tonomura et al. ............. | 606/185 |
| 5,817,060 | A * | 10/1998 | Overton et al. .......... | 604/164.01 |
| 6,203,533 | B1 * | 3/2001 | Ouchi ........................... | 604/264 |
| 6,258,064 | B1 * | 7/2001 | Smith et al. .............. | 604/164.12 |
| 7,147,607 | B2 * | 12/2006 | Wang ............................. | 600/566 |
| 2002/0032372 | A1 * | 3/2002 | Ouchi ........................... | 600/182 |
| 2003/0195471 | A1 * | 10/2003 | Woehr et al. ............. | 604/164.08 |
| 2005/0090763 | A1 * | 4/2005 | Wang ............................. | 600/564 |

FOREIGN PATENT DOCUMENTS

| | | | |
|---|---|---|---|
| JP | 63-34699 | 9/1988 | |
| JP | 06-304132 | * 1/1994 | ............... A61B 1/00 |
| JP | 06-304132 | 11/1994 | |
| JP | 09-084874 A | 3/1997 | |

(Continued)

OTHER PUBLICATIONS

English translation of JP 10211279 (identified as JP,10-211279,A(1998) on the translation).*

(Continued)

*Primary Examiner* — Kevin C Sirmons
*Assistant Examiner* — Imani Hayman
(74) *Attorney, Agent, or Firm* — Ostrolenk Faber LLP

(57) ABSTRACT

A puncture needle for an endoscope includes: a flexible sheath; a needle component that is placed on an interior side of the sheath such that it can move freely forwards and backwards; a wire that is provided at a base end portion of the needle component, and that moves the needle component forwards or backwards along an axial direction of the sheath; and an operating section that is connected to an operating side of the sheath, and operates the wire. This wire is formed by a metal material that has elasticity, and a bent portion is provided in the wire that generates friction against an inner wall of the operating section, and imparts resistance to the forwards and backwards movement of the needle component.

15 Claims, 3 Drawing Sheets

(56) References Cited

FOREIGN PATENT DOCUMENTS

| JP | 10-015062 A | | 1/1998 |
|---|---|---|---|
| JP | 10211279 | * | 8/1998 |
| JP | 10211279 A | * | 8/1998 |
| JP | 10-277149 | | 10/1998 |
| JP | 2001-46500 | | 2/2001 |
| JP | 2001-514943 | | 9/2001 |
| JP | 3548300 | | 4/2004 |
| JP | 2004-513686 | | 5/2004 |
| JP | 2005-52408 | | 3/2005 |
| WO | 02/28466 | | 4/2002 |

OTHER PUBLICATIONS

PCT International Search report dated Feb. 14, 2006 issued in corresponding PCT Application No. PCT/JP2005/020418.
PCT International Written Opinion dated Feb. 14, 2006 issued in corresponding PCT Application No. PCT/JP2005/020418.
European Search Report dated Apr. 7, 2010.

* cited by examiner

PUNCTURE NEEDLE FOR ENDOSCOPE

TECHNICAL FIELD

The present invention relates to a puncture needle for an endoscope that is used by being inserted into a treatment tool insertion channel in an endoscope.

Priority is claimed on Japanese Patent Application No. 2004-369573, filed Dec. 21, 2004, the contents of which are incorporated herein by reference.

BACKGROUND ART

An injection tool for an endoscope is disclosed, for example, in Japanese Unexamined Patent Application, First Publication No. 6-304132. In this injection tool for an endoscope, a slender injection needle is placed inside a pallial tube such that it can be moved freely forwards and backwards. When this injection tool is used, firstly, a distal end of the injection needle is retracted into the interior of the pallial tube and, in this state, the injection tool is inserted into the treatment tool insertion channel of an endoscope. When the distal end of the injection tool protrudes from the distal end of the insertion portion of the endoscope, the injection needle is pushed out from the distal end of the pallial tube so that it pierces an abdominal cavity wall. At this time, sliding resistance (i.e., friction resistance) is imparted to the operating section so that the injection needle is anchored relative to the pallial tube. Specifically, a rubber rod is placed in a Luer cap that extends in a direction that is orthogonal to the operating section, so that sliding resistance is generated in the stylet.

Moreover, in Japanese Patent No. 3548300 an injection tool for an endoscope is disclosed in which a pipe material is bent inside an operating section so that sliding resistance is obtained from a liquid feed tube.

DISCLOSURE OF INVENTION

It is an object of the present invention to provide a puncture needle for an endoscope that makes it possible to prevent a needle from accidentally protruding.

The puncture needle for an endoscope of this invention includes: a flexible sheath; a needle component that is placed on an interior side of the sheath such that the needle component moves forwards and backwards; a needle moving device that is provided at a base end portion of the needle component, and that moves the needle component forwards or backwards along an axial direction of the sheath; and an operating section that is connected to an operating side of the sheath, and operates the needle moving device. In addition, the needle moving device is formed by a metal wire that has elasticity, and a bent portion is provided in the wire that generates friction against an inner circumferential surface of the operating section, and imparts resistance to the forwards and backwards movement of the needle component.

Moreover, in order to solve the above described problems, the puncture needle for an endoscope of this invention includes: a flexible sheath; a tube-shaped needle component that is placed on an interior side of the sheath such that the needle component moves forwards and backwards in an axial direction of the sheath; an operating wire that is provided at a base end portion of the needle component, and that moves the needle component forwards or backwards as the operating wire moves itself forwards or backwards; a protective device that is provided at a distal end portion of the sheath and protects a sharp portion of the needle component; aperture portions that are provided at both a distal end portion and the base end portion of the needle component, and that allow air to enter and exit the interior and exterior of the needle component; and an operating cap that is provided at a base end portion of the sheath, and that causes air to enter and exit an internal space of the sheath and the needle component. In addition, the wire is provided with a straight portion and a bent portion that has elasticity.

Moreover, preferably, the bent portion is provided in from one to three locations in the wire.

The puncture needle for an endoscope of this invention includes: a flexible sheath; a needle component that is placed on an interior side of the sheath such that the needle component moves forwards and backwards; a needle moving device that is provided at a base end of the needle component, and that moves the needle component forwards or backwards along an axial direction of the sheath; an operating section that is connected to an operating side of the sheath, and operates the needle moving device; an elastic portion that is provided at a base end side of the needle moving device, and is provided so as to press an inner wall of the operating section; and a space that joins together a space at the distal end side of the elastic portion with a space at the base end side of the elastic portion.

BEST MODE FOR CARRYING OUT THE INVENTION

Best embodiments for implementing this invention (referred to below as 'the embodiments') are described below with reference made to the drawings.

Firstly, a first embodiment will be described using FIGS. 1A and 1B and FIG. 2.

Figure 1A:
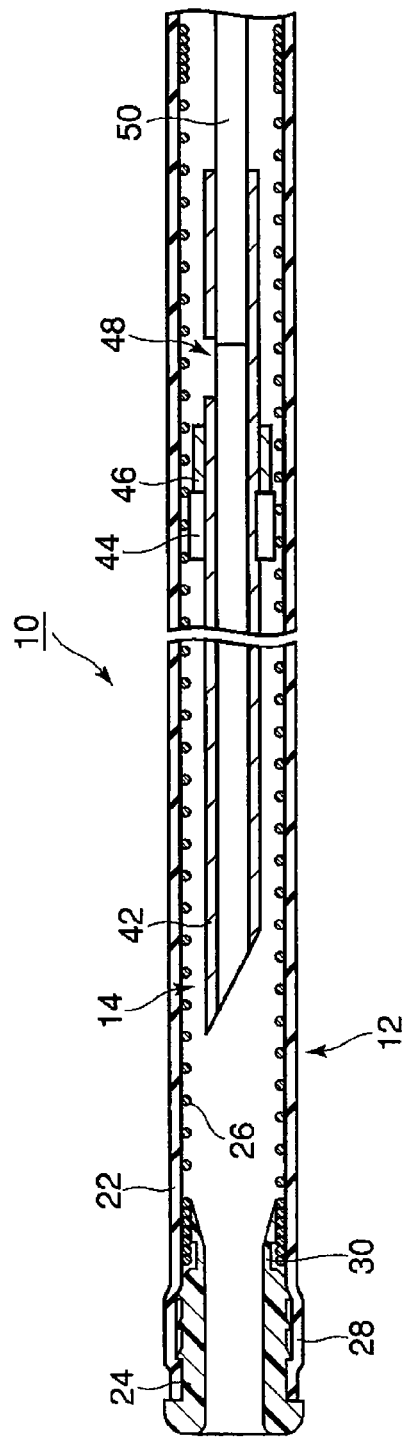
FIG. 1A is a schematic cross-sectional view showing a puncture needle for an endoscope according to a first embodiment, and shows a sheath and needle component on a distal end portion side.
Figure 1B:
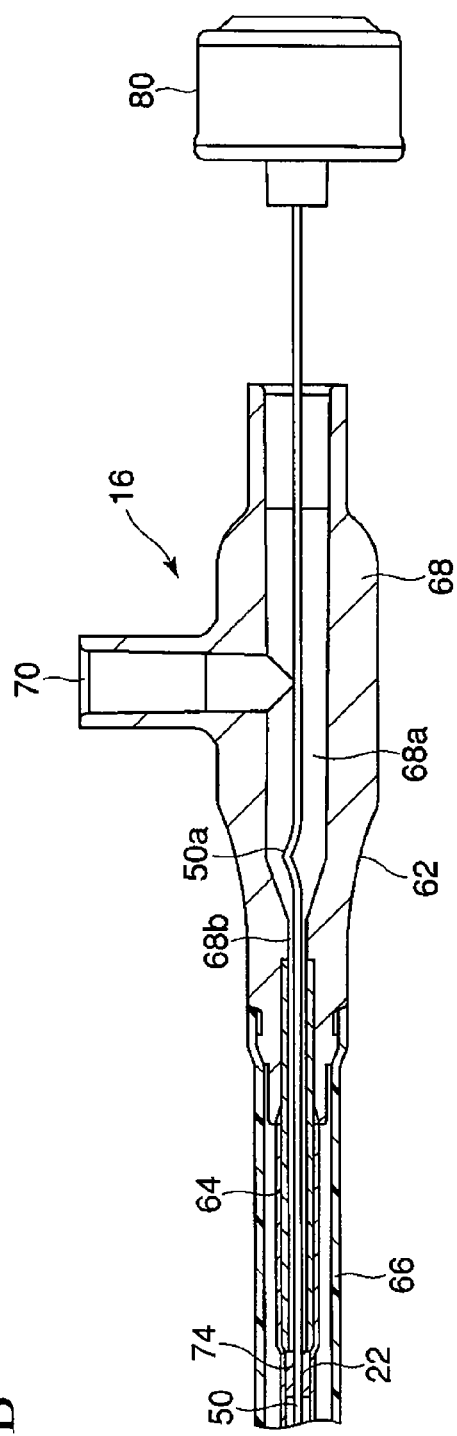
FIG. 1B is a schematic cross-sectional view showing a puncture needle for an endoscope according to the first embodiment, and shows an operating portion side of a base end portion.
Figure 2:
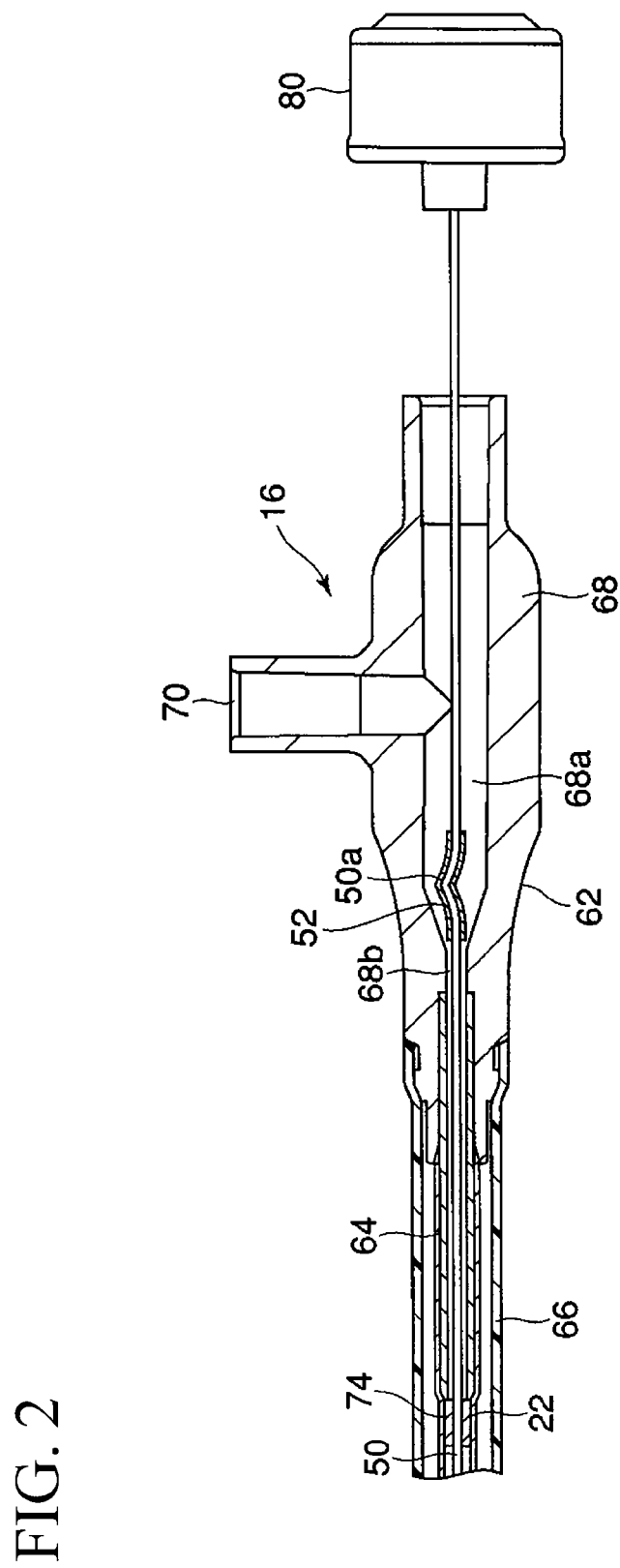
FIG. 2 is a schematic cross-sectional view showing an operating portion side of a base end portion of a puncture needle for an endoscope according to a second embodiment.

As is shown in FIGS. 1A and 1B and FIG. 2, a puncture needle 10 for an endoscope according to this embodiment is provided with a narrow elongated sheath 12, a tube-shaped needle component 14 that is able to move forwards and backwards inside this sheath 12, and an operating section 16 that is provided at a base end side of the sheath 12 and moves the needle component 14 relative to the sheath 12.

As is shown in FIG. 1A, the sheath 12 is provided with a sheath body 22, a stopper 24, and protective components 26.

The stopper 24 which has an inner diameter that allows a distal end portion of the needle component 14 to protrude therefrom is fitted onto a distal end portion of the sheath body 22. At the distal end portion of the sheath body 22, this stopper 24 covers the distal end of the sheath body 22 and the inner circumferential surface thereof. A projection 28 is formed on an outer circumferential surface of the stopper 24 that is used to fix the stopper 24 to the inner circumferential surface of the sheath body 22. A holding portion 30 that holds distal end portions of the protective components 26 in a state of being nipped between the stopper 24 and the sheath body 22 is formed on a base end portion of the stopper 24.

The protective components 26 that protect the distal end portion of the needle component 14 are located on a base end portion of the stopper 24. These protective components 26 are mounted on the inner circumferential surface of the sheath body 22.

The needle component 14 is provided with a needle component body 42, a sealing component 44, and an anchoring component 46.

The needle component body 42 is hollow and is formed having a sharp distal end. Namely, an aperture portion is formed at the distal end of the needle component body 42.

The sealing component 44 is ring shaped, and is mounted on an outer circumferential surface of the base end portion of the needle component body 42. This sealing component 44 is able to slide against the inner circumferential surface of the protective component 26 of the sheath 12. When the sealing component 44 is placed hard against the inner circumferential surface of the stopper 24, the airtightness from the sealing component 44 towards the base end portion side is maintained.

The anchoring component 46 is ring shaped and is mounted on the outer circumferential surface of the base end portion of the needle component body 42. This anchoring component 46 is also placed on a base end portion of the sealing component 44. The anchoring component 46 is able to slide against the inner circumferential surface of the protective component 26 of the sheath 12. The anchoring component 46 is positioned so as to limit the length of the protruding portion when the distal end of the needle component body 42 protrudes from the distal end of the sheath 12. As a result, the length of the protruding portion of the needle component body 42 is prescribed by the position of the anchoring component 46.

Furthermore, an aperture portion 48 is formed on the needle component body 42 on the base end portion side down from the anchoring component 46. This aperture portion 48 connects the interior of the needle component body 42 with the exterior thereof.

A wire (i.e., a needle moving device) 50 made, for example, from stainless steel is connected in a gripped state to the needle component body 42 on the rear end portion side down from the aperture portion 48 and on the same axis therewith. This wire 50 passes through the sheath 12 and the operating section 16 and extends beyond there towards the operator.

As is shown in FIG. 1B, the operating section 16 is provided with an operating section body 62, a connecting component 64, and a bend prevention component 66.

The operating section body 62 is provided with a circular cylinder portion 68 through which the wire 50 is inserted, and a Luer cap 70 that is formed extending in an orthogonal direction relative to the circular cylinder portion 68 and that is fitted with a syringe (not shown). The circular cylinder portion 68 is provided with a large diameter hole portion 68a whose inner diameter has a large diameter hole, and a small diameter hole portion 68b whose inner circumferential surface is formed having a smaller diameter than the inner diameter of the large diameter hole portion 68a. The large diameter hole portion 68a is located on the base end portion side of the circular cylinder portion 68, while the small diameter hole portion 68b is located on the distal end portion side of the circular cylinder portion 68 and on the center axis of the large diameter hole portion 68a. The large diameter hole portion 68a and the small diameter hole portion 68b are smoothly connected, for example, by a tapered portion or the like.

The connecting component 64 is located on the inner circumferential surface of the distal end portion of the small diameter hole portion 68b of the circular cylinder portion of the operating section body 62. A base end portion of the sheath 12 is fitted onto an outer circumferential surface of the connecting component 64. A base end of the sheath body 22 of the sheath 12 is fitted such that it abuts against the distal end of the circular cylinder 68.

The bend prevention component 66 is connected to the distal end portion of the operating section body 62 and covers the base end portion of the sheath 12. Because this bend prevention component 66 is formed from a hard resin material, it is possible to prevent a large force being applied to the sheath 12 or wire 50 by the distal end portion of the operating section 16.

The wire 50 is provided with a position restricting component 74 on the distal end side of the connecting component 64 of the operating section 16 that restricts movement of a dial 80 (described below) in a direction away from the base end portion of the operating section 16.

A single bent portion (i.e., an elastic portion) 50a is formed in the wire 50 that is located inside the circular cylinder portion 68 of the operating section 16. Namely, the wire 50 is provided with straight portions on both the distal end portion side and base end portion side of the bent portion 50a. This single bent portion 50a is formed so that, when the bent portion 50a moves from the large diameter hole portion 68a to the small diameter hole portion 68b, it presses against the wall portion of the hole portion 68b and thereby generates sliding resistance. In this embodiment, the single bent portion 50a is formed such that the angle of the apex point thereof is between, for example, 120 degrees and 170 degrees, or is formed substantially in a mountain shape such as substantially in a circular arc shape. Note that, even when the connecting component 64 and the bent portion 50a are connected, a gap (i.e., a space) is still present within the connecting component 64 that allows a fluid to flow from the distal end to the base end thereof.

The dial 80 which is operated by an expert is mounted on a base end portion of the wire 50. An elastic component that is formed from a resin material which is capable of blocking the connected state between the internal portion and external portion of the circular cylinder portion 68 when the dial 80 is joined to the circular cylinder portion 68 of the base end portion of the operating section 16 is provided at the distal end of the dial 80. This dial 80 is able to move between a state in which it is joined to the circular cylinder portion 68 at the base end portion of the operating section 16 and a position where the above described position restricting component 74 is in contact with the distal end of the connecting component 64. Namely, the wire 50 is able to move backwards and forwards only within a predetermined range.

Next, operations of the puncture needle 10 for an endoscope of this embodiment will be described.

The distal end of the needle component 14 of the puncture needle 10 for an endoscope is left in a retracted state relative to the distal end of the sheath 12. At this time, the bent portion 50a of the wire 50 is located in the large diameter hole portion 68a of the circular cylinder portion 68 of the operating section 16.

The distal end portion of the insertion portion of the endoscope is placed in the vicinity of a target position such that it faces the target position.

In this state, the puncture needle 10 for an endoscope is inserted from the distal end of the sheath 12 through the treatment tool insertion channel that is provided in the insertion portion of the endoscope. The distal end of the sheath 12 is then made to protrude from the distal end surface of the insertion portion. At this time, the bent portion 50a of the wire 50 is prevented from entering the small diameter hole portion 68b of the circular cylinder 68 of the operation section 16 by the sliding resistance generated by the elastic deformation of the bent portion 50a. As a result, the distal end of the needle component body 42 is prevented from protruding from the distal end of the sheath 12.

The dial 80 is then moved so as to approach the base end portion of the operating section 16, and the needle component body 42 is made to protrude from the distal end of the sheath 12. At this time, the sealing component 44 of the needle component 14 abuts against the stopper 24 while being elastically deformed, and the anchoring component 46 also abuts against the stopper 24. At this time, the dial 80 is mounted on the base end portion of the operating section 16. At this time, the bent portion 50a of the wire 50 is located in the small diameter hole portion 68b of the circular cylinder portion 68 of the operating section 16.

As a result, a state is maintained in which the internal space of the needle component body 42 is in communication with the Luer cap 70 of the operating section 16, however, in this state the outer circumferential surface on the distal end portion side of the needle component body 42 is also cut off from the operating section 16 side.

The distal end of the needle component body 42 then punctures the target position.

In this state, a syringe (not shown) is mounted in the Luer cap 70 of the operating section 16 and suctioning is performed. At this time, because the circular cylinder portion 68 of the operating section 16 is in communication with the internal space of the sheath 12, the circular cylinder portion 68 of the operating section 16 and the internal space of the sheath 12 are depressurized. As a result, the internal space inside the needle component body 42 is depressurized via the aperture portion 48 of the needle component body 42. Consequently, biological tissue is suctioned so as to be placed inside the internal space of the needle component body 42.

After the suctioning, the syringe is removed from the Luer cap 70 of the operating section 16. The dial 80 is moved in a direction away from the operating section 16, and the distal end of the needle component body 42 is once again placed inside the distal end of the sheath 12. In this state, the puncture needle 10 for an endoscope is pulled out from the treatment tool insertion channel of the endoscope. At this time, the bent portion 50a of the wire 50 is placed in the large diameter hole portion 68a. As a result, the bent portion 50a is prevented from entering the small diameter hole portion 68b of the circular cylinder portion 68 of the operating section 16 by the sliding resistance generated by the elastic deformation of the bent portion 50a. As a result, the distal end of the needle component body 42 is prevented from protruding from the distal end of the sheath 12.

In the puncture needle 10 for an endoscope which has been extracted from the treatment tool insertion channel, the needle component body 42 is then made to protrude from the distal end of the sheath 12 by once again moving the dial 80 such that it approaches the base end portion of the operating section 16. At this time, the dial 80 is fitted on the base end portion of the operating section 16.

Pressurized air is then fed from the Luer cap 70, and the biological tissue that is contained inside the needle component body 42 is extracted to the outside (i.e., is recovered) from the distal end of the needle component body 42. Various examinations can then be made on the biological tissue that has been extracted in this manner.

As has been described above, according to the puncture needle 10 for an endoscope of this embodiment, the following effects are obtained.

Because the bent portion 50a is formed in the operating wire 50, due to the sliding resistance of the bent portion 50a to the inner circumferential surface between the large diameter hole portion 68a and the small diameter hole portion 68b, and to the inner circumferential surface of the small diameter hole portion 68b, it is possible to prevent the needle component 14 that is connected to the distal end of the wire 50 protruding by accident beyond the distal end of the sheath 12. As a result, it is possible to prevent any incorrect puncturing by the distal end of the needle component body 42, and it is also possible to prevent the treatment tool insertion channel in the endoscope being damaged by the distal end of the needle component body 42. Moreover, because there is a gap (i.e., a space) between the connecting component 64 and the bent portion 50a even in a state in which the needle component 14 is protruding from the distal end of the stopper 24, it is possible without sealing the suctioning tube to maintain a state in which suctioning of biological tissue is always possible.

Next, a second embodiment will be described using FIG. 2. This embodiment is a variant example of the puncture needle 10 for an endoscope of the first embodiment. The same symbols are used for component elements that are the same as those described in the first embodiment, and a detailed description thereof is omitted.

As is shown in FIG. 2, a heat contraction tube 52 which contracts when heat is applied thereto covers the bent portion 50a of the wire 50 for an endoscope according to this embodiment. This heat contraction tube 52 is molded, for example, from a fluorine resin material.

When the wire 50 and the connecting component 64 are both formed from a metal material, there may be cases in which a sensation of roughness is generated when the two metal materials come into contact with each other. In a case such as this, because slidability is achieved between the resin material and the metal material by covering the outer circumference of the bent portion 50a with the heat contraction tube 52, sliding resistance between the heat contraction tube 52 on the outer circumference of the bent portion 50a and the connecting component 64 is reduced and smoothness is achieved.

Accordingly, by covering the outer side of the bent portion 50a with the above described heat contraction tube 52, it is possible to alleviate or eliminate any sensation of roughness.

Next, a third embodiment will be described using FIG. 3. This embodiment is a variant example of the puncture needle 10 for an endoscope of the first embodiment. The same symbols are used for component elements that are the same as those described in the first embodiment, and a detailed description thereof is omitted.

Figure 3:
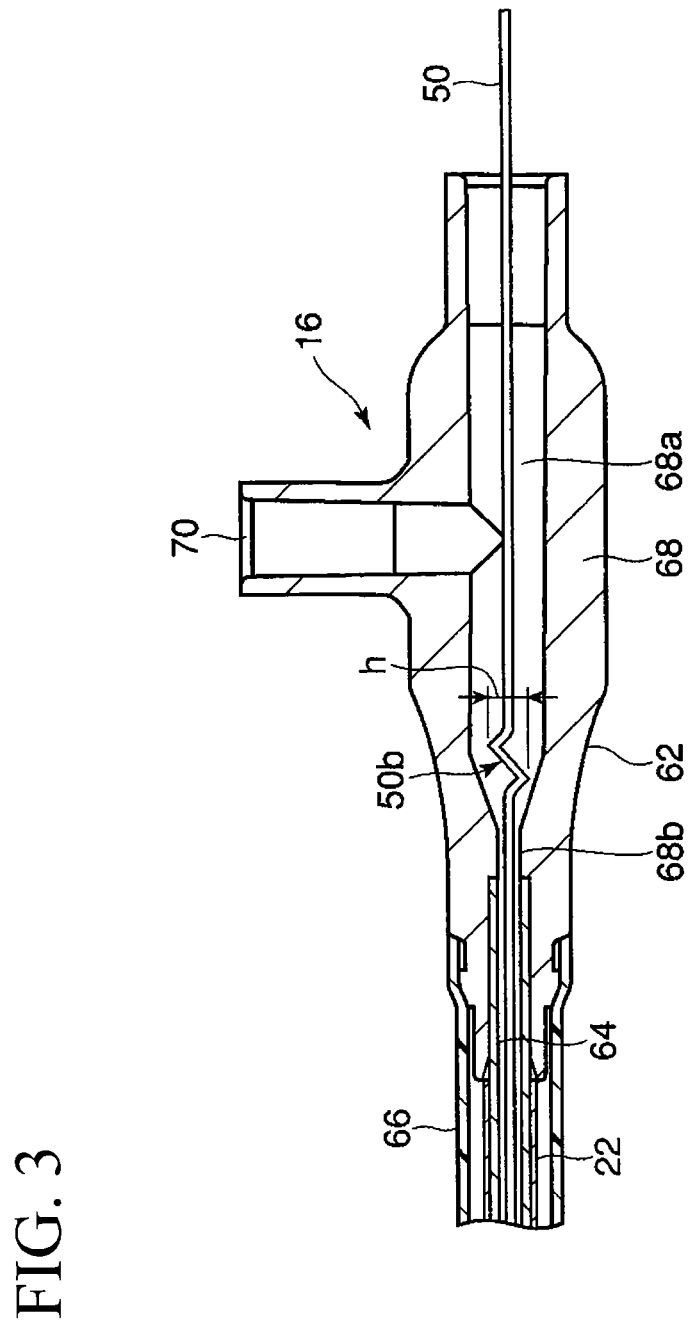
FIG. 3 is a schematic cross-sectional view showing an operating portion side of a base end portion of a puncture needle for an endoscope according to a third embodiment.

As is shown in FIG. 3, the puncture needle 10 for an endoscope according to this embodiment differs from the puncture needle 10 for an endoscope described in the first embodiment in the fact that the shape of the bent portion 50a of the wire 50 is modified in the manner shown by the symbol 50b.

The bent portion 50b is formed in the wire 50 that is contained in the large diameter hole portion 68a of the circular cylinder portion 68 of the operating section 16. This bent portion 50b is bent a plurality of times so as to be formed, for example, in a wave shape having a single wavelength within the same plane. A distance h between the end portions of the bent portion 50b that are furthest from the axial direction of the wire 50, which corresponds to the amplitude of the wavelength at this time, is formed so as to be larger than the diameter of the small diameter hole portion 68b.

Because the action of the puncture needle 10 for an endoscope according to this embodiment is the same as that of the puncture needle 10 for an endoscope described in the first embodiment, a description thereof is omitted.

According to the puncture needle 10 for an endoscope of this embodiment, the following effects are obtained.

Because the bent portion 50b that is bent a plurality of times is provided in the operating wire 50 so that the operating wire 50 overall can be formed substantially in a completely straight state, when the dial 80 is held and wire 50 is moved forwards or backwards, it can be moved completely straightly relative to the sheath 12 and the operating section 16.

Note that it is favorable for the heat contract tube 52 (see FIG. 2) described in the second embodiment to also be used for the bent portion 50b described in this embodiment.

Moreover, in the above described first through third embodiments, a structure is described in which the bent portions 50a and 50b are only provided in one location on the wire 50, however, bent portions may also be favorably provided in a plurality of positions such as in two or three locations.

Hitherto, a number of embodiments have been specifically described with reference made to the drawings, however, the present invention is not limited to the above described embodiment and includes all embodiments that do not depart from the spirit or scope of the present invention.

As is clear from the above description, the puncture needle for an endoscope of the present invention includes: a flexible sheath; a needle component that is placed on an interior side of the sheath such that it can move freely forwards and backwards; a needle moving device that moves the needle component; and an operating section that is connected to an operating side of the sheath. In this puncture needle, the needle moving device is formed by a metal wire that has elasticity, and a bent portion is provided in the wire that generates friction against an inner circumferential surface of the operating section, and imparts resistance to the forwards and backwards movement of the needle component.

Moreover, the puncture needle for an endoscope of the present invention includes: a flexible sheath; a needle component that is placed on an interior side of the sheath such that it can move freely forwards and backwards; an operating wire that moves the needle component forwards or backwards; a protective device that is provided at a distal end portion of the sheath and protects a sharp portion of the needle component; aperture portions of which at least one is provided at a distal end portion of the needle component, and of which at least another one is provided at the base end portion of the needle component; and an operating cap that is provided at a base end portion of the sheath, and that causes air to enter and exit an internal space of the sheath and the needle component. In this puncture needle for an endoscope, it is also possible to employ a structure in which the wire is provided with a straight portion and a bent portion that has elasticity, and the bent portion generates sliding resistance between itself and the internal space inside the operating cap so that resistance is imparted to the needle component when it is moved.

It is also possible for the bent portion to be provided in from one to three locations on the wire.

It is also possible for the bent portion to be formed in a circular arc shape.

It is also possible for the bent portion to be bent at an angle of between 120 degrees and 170 degrees.

It is also possible for the bent portion to have a resin material on an outer circumference thereof.

In the puncture needle for an endoscope according to this invention, because it is possible for sliding resistance to be imparted inside the operating section by the bend in the wire, it is possible to obtain consistent sliding resistance irrespective of the bent state of the sheath and the like.

Moreover, in the present invention, the bent portion generates sliding resistance between itself and the internal space inside the operating cap so that resistance can be imparted to the movement of the needle component in the axial direction of the sheath. Accordingly, it is possible to obtain consistent sliding resistance irrespective of the bent state of the sheath and the like.

Moreover, it is preferable for the bent portion to be provided in from one to three locations on the wire.

As a result, by forming, for example, a plurality of bent portions, it is possible to obtain a more consistent sliding resistance.

Moreover, in the present invention, because the elastic portion that is provided at the base end side of the needle moving device is provided such that it is pressed against the internal wall of the operating section, not only is it possible to obtain consistent sliding resistance irrespective of the bent state of the sheath and the like, but it is also possible to constantly maintain a state in which biological tissue can be suctioned without sealing the suction tube.

The present invention can be applied to a puncture needle for an endoscope that makes it possible to prevent a needle component from accidentally protruding.

The invention claimed is:

1. A puncture needle for an endoscope, the puncture needle comprising:
    a flexible sheath having an interior;
    a needle component positioned at the interior of the flexible sheath such that the needle component is free to move forwards and backwards;
    a needle moving device positioned at a base end portion of the needle component, and configured to move the needle component forwards or backwards along an axial direction of the flexible sheath; and
    an operating section connected to the operating side of the flexible sheath, and configured to operate the needle moving device,
    wherein the operating section comprises a hole portion composed of a small diameter hole portion, a large diameter hole portion and a connecting section which is positioned between the small diameter hole portion and the large diameter hole portion;
    the needle moving device comprises a metal wire which is inserted into the sheath and the operating section and which has elasticity,
    the metal wire comprises a straight portion and an elastic portion having a diameter larger than a diameter of the straight portion;
    the needle component is configured such that a distal end thereof does not protrude from a distal end of the sheath in a state in which the elastic portion is not positioned in the small diameter hole portion, and
    the elastic portion is configured to generate slide friction before the elastic portion enters into the small diameter hole portion by pressing an inner periphery of the connecting section when the elastic portion moves from the large diameter hole portion to the small diameter hole portion such that the needle component is prevented from carelessly protruding from the distal end of the sheath.

2. The puncture needle for an endoscope according to claim 1, wherein the elastic portion is provided in from one to three locations.

3. The puncture needle for an endoscope according to claim 1, further comprising a tapered portion positioned between a large diameter inner circumferential surface and a small diameter inner circumferential surface in the operating section.

4. The puncture needle for an endoscope according to claim 3, wherein a small diameter portion of the tapered portion is directed toward a distal end portion of the needle component and a large diameter portion of the tapered portion is directed toward the base end portion of the needle component.

5. The puncture needle for an endoscope according to claim 1, wherein the elastic portion comprises a resin material on an outer circumference thereof.

6. The puncture needle for an endoscope according to claim 1, wherein the connecting section is a tapered portion connecting the small diameter hole portion with the large diameter hole portion.

7. A puncture needle for an endoscope, the puncture needle comprising:
a flexible sheath having an interior;
an operating section connected to an operating side of the flexible sheath and configured to operate a needle moving device;
a tube-shaped needle component having a base end and comprising a ring-shaped sealing component mounted thereon, the tube-shaped needle component positioned at the interior of the flexible sheath such that the needle component is free to move forwards and backwards in an axial direction of the flexible sheath;
an operating wire positioned at a base end portion of the needle component and configured to move the needle component forwards or backwards in response to a forward or backward movement of the operating wire;
protective components mounted on an inner circumferential surface of the flexible sheath, the protective components being spaced in the axial direction of the flexible sheath along an entire length of travel of the ring-shaped sealing component;
aperture portions positioned at both a distal end portion and the base end portion of the needle component, and configured to allow air to enter and exit the interior and exterior of the needle component; and
an operating cap positioned at a base end portion of the flexible sheath, and configured to cause air to enter and exit an internal space of the sheath and the needle component,
wherein the operating section comprises a hole portion composed of a small diameter hole portion, a large diameter hole portion and a connecting section which is positioned between the small diameter hole portion and the large diameter hole portion;
the operating wire comprises a straight portion and an elastic portion having a diameter larger than a diameter of the straight portion;
hole portion provided in a distal end portion side of the operating section;
the needle component is configured such that a distal end thereof does not protrude from a distal end of the sheath in a state in which the elastic portion is not positioned in the small diameter hole portion, and
the elastic portion is configured to generate slide friction before the elastic portion enters into the small diameter hole portion by pressing an inner periphery of the connecting section when the elastic portion moves from the large diameter hole portion to the small diameter hole portion such that the needle component is prevented from carelessly protruding from the distal end of the sheath.

8. The puncture needle for an endoscope according to claim 7, wherein the elastic portion is provided in from one to three locations.

9. The puncture needle for an endoscope according to claim 7, further comprising a tapered portion positioned between the large diameter hole portion and the small diameter hole portion in an operating section.

10. The puncture needle for an endoscope according to claim 9, wherein a small diameter portion of the tapered portion is directed toward the distal end portion of the needle component and a large diameter portion of the tapered portion is directed toward the base end portion of the needle component.

11. The puncture needle for an endoscope according to claim 7, wherein the elastic portion comprises a resin material on an outer circumference thereof.

12. A puncture needle for an endoscope comprising:
a flexible sheath having an interior;
a needle component positioned at an interior of the flexible sheath such that the needle component is free to move forwards and backwards;
a needle moving device positioned at a base end of the needle component, and configured to move the needle component forwards or backwards along an axial direction of the flexible sheath;
an operating section connected to the operating side of the flexible sheath and being configured to operate the needle moving device;
an elastic portion positioned at the base end side of the needle moving device; and
a space that joins together a space at the distal end side of the elastic portion with a space at the base end side of the elastic portion;
wherein the operating section
comprises a hole portion composed of a small diameter hole portion, a large diameter hole portion and a tapered portion which is positioned between the small diameter hole portion and the large diameter hole portion
an outer surface of the elastic portion is covered with a resin tube;
the needle component is configured such that a distal end thereof does not protrude from a distal end of the sheath in a state in which the elastic portion is not positioned in the small diameter hole portion, and
the elastic portion is configured to generate slide friction before the elastic portion enters into the small diameter hole portion by pressing an inner periphery of the connecting section when the elastic portion moves from the large diameter hole portion to the small diameter hole portion such that the needle component is prevented from carelessly protruding from the distal end of the sheath.

13. The puncture needle for an endoscope according to claim 12, wherein the small diameter hole portion is directed toward a distal end portion of the needle component and the large diameter hole portion is directed toward the base end portion of the needle component.

14. The puncture needle for an endoscope according to claim 12, wherein a predetermined shape of the elastic portion includes an apex of the elastic portion between 120 and 170 degrees.

15. The puncture needle for an endoscope according to claim 12, wherein a predetermined shape of the elastic portion includes the elastic portion having a substantial circular arc shape.

\* \* \* \* \*